United States Patent [19]

Hammond

[11] 3,976,656

[45] Aug. 24, 1976

[54] 1,4-BIS(5-p-n-BUTOXYPHENYLOXAZOL-2-YL)BENZENE AND THE PREPARAION THEREOF

[75] Inventor: Peter R. Hammond, China Lake, Calif.

[73] Assignee: The United States of America as represented by the Secretary of the Navy, Washington, D.C.

[22] Filed: Jan. 20, 1975

[21] Appl. No.: 542,151

[52] U.S. Cl. ........................ 260/307 R; 260/248.5; 260/558 R; 260/567.6 M; 260/590 R; 331/94.5 L

[51] Int. Cl.[2] ........................ C07D 263/32

[58] Field of Search ......... 260/590 R, 307 R, 248.5, 260/567.6 M, 558 R

[56] References Cited

UNITED STATES PATENTS

| | | | |
|---|---|---|---|
| 2,726,246 | 12/1955 | Trosken et al. | 260/302 |
| 3,148,194 | 9/1964 | Waugh et al. | 260/307 |

*Primary Examiner*—Nicholas S. Rizzo
*Assistant Examiner*—D. B. Springer
*Attorney, Agent, or Firm*—R. S. Sciascia; Roy Miller; David J. Aston

[57] ABSTRACT

1,4-Bis(5-p-n-butoxyphenyloxazol-2-yl)-benzene is prepared. The compound is useful as a lasing dye.

2 Claims, No Drawings

1,4-BIS(5-p-n-BUTOXYPHENYLOXAZOL-2-YL)BENZENE AND THE PREPARAION THEREOF

BACKGROUND OF THE INVENTION

1. Field of the Invention.

This invention relates to dyes which are useful as lasing materials.

2. Description of the Prior Art.

Those interested in the laser field are interested in materials which will lase. The present invention relates to a dye which will lase. Insofar as is known to the inventor, the dye disclosed herein has never been prepared before.

SUMMARY OF THE INVENTION

The dye disclosed herein is 1,4-bis(5-p-n-butoxyphenyloxazol-2-yl)-benzene. It is prepared by (1) brominating p-n-butoxyacetophenone to form p-n-butoxyphenacyl bromide, (2) reacting p-n-butoxyphenacyl bromide with hexamethylene tetramine to form a quaternary salt, (3) reacting the quaternary salt with hydrochloric acid to form p-n-butoxyphenacylammonium chloride, (4) reacting the chloride with terephthaloyl chloride to form N,N'-di-p-n-butoxyphenacylterephthalimide, and (5) reacting the imide with phosphoryl chloride to form the final compound.

DESCRIPTION OF THE PREFERRED EMBODIMENT

The preparation of 1,4-bis(5-p-n-butoxyphenyloxazol-2-yl)-benzene and its intermediates is disclosed as follows. The starting material in the preparation is p-n-butoxyacetophenone.

Quaternary salt from p-n-Butoxyphenacyl Bromide and Hexamethylene Tetramine To a stirred solution of p-n-butoxyacetophenone (23.0 g) in ethyl ether (200 ml), bromine was added. First, 0.6 ml of bromine was added and the solution was stirred until the bromine color vanished. Then another 1.0 ml was added and the solution was again stirred until the bromine color disappeared. Finally, 5.0 ml of bromine was added over a period of 5 minutes followed by 10 minutes of stirring. The pale yellow solution obtained at the end of the bromine additions was washed twice with water, dried overnight with sodium sulfate and evaporated to a colorless, mobile gum. A nuclear magnetic resonance spectrum was obtained and indicated 85% conversion to p-n-butoxyphenacyl bromide.

All of the p-n-butoxyphenacyl bromide was dissolved in chloroform (60 ml) and hexamethylene tetramine (14.0 g) in chloroform (15 ml) was added. The mixture immediately warmed but, after 3 hours, deposited only a few milligrams of material. A precipitate was produced by dropping the solution slowly into a large excess (600 ml) of rapidly stirred ether. The thus produced precipitate was filtered and washed with water. Analysis of the precipitate showed that it was a quaternary salt of p-n-butoxyphenacyl bromide and hexamethylene tetramine. Calculated for $C_{18} H_{27} N_4 0_2 Br$: C 52.6; H 6.57; N 13.64 and Br 19.43%. Found: C 52.89, 52.66; H 6.77, 6.85; N 13.52, 13.54 and Br 19.67, 19.38%. The quaternary salt melted at from 127° to 128°C. The nuclear magnetic resonance spectrum in deuterochloroform on a Varian XL-100-15 spectrometer showed triplets at $\delta$ values 1.00 and 3.98 ($—CH_2 CH_3$ and $OCH_2CH_2—$) along with a broad absorption 1.1 to 2.1 (aliphatic $—CH_2—$ chain), a singlet at 5.50 ($—COCH_2—N+$) and an aromatic $A_2 B_2$ spectrum at 6.82, 6.92, 8.00 and 8.09. The hexamethylene tetramine signal was split into a singlet at 5.99, 6 protons [$-N \overset{+}{\equiv} (CH_2)_3, \equiv$] and an AB quartet centered at 4.70, 6 protons [$\equiv N_3(CH_2)_3$] with a coupling constant of 14 cycles between the axial and equatorial protons. A yield of 40.5 g (near quantitative) of the salt was obtained. It could be used directly in the next stage of the preparation or could be crystallized from a large volume of acetone.

N,N'-di-p-n-Butoxyphenacylterephthalimide

The hexamethylene tetramine quaternary salt of p-n-butoxyphenacyl bromide (40.0 g) was stirred vigorously in ethanol (320 ml) and concentrated hydrochloric acid (40 ml) was added. The reaction mixture was allowed to stand overnight and deposited a large quantity of solid. More ethanol (250 ml) was added. After 60 more hours the reaction mixture was warmed gently and filtered. The precipitate was washed with 50 ml of warm ethanol. p-n-Butoxyphenacylammonium chloride (20.1 g — 85% yield) was precipitated as a white powder by slowly dropping the alcohol solution into 3.0 l of dry ether. The precipitate was filtered and dried. The nuclear magnetic resonance spectrum in deuterium oxide at 60°C on a Varian A-60 spectrometer showed triplets centered at 1.10 and 4.05 ($—CH_2 CH_3$ and $—O CH_2CH_2—$), an aromatic $A_2B_2$ system at 6.80, 6.95, 7.75 and 7.90, a singlet at 4.68 ($—CO CH_2N—$) and a broad absorption around 1.70 (aliphatic $—CH_2—$ chain). Integrated intensities were in accord with the structure of p-n-butoxyphenacylammonium chloride. p-n-Butoxyphenacylammonium chloride (20.0 g) and terephthaloyl chloride (8.0 g) were refluxed in dry pyridine (150 ml) in the absense of moisture for one hour. The mixture was then cooled and poured, with stirring, into water (500 ml) and the solid was filtered, washed with water, dried and recrystallized from 500 ml of pyridine. A white crystalline solid (7.7 g — 35% yield) was obtained. The solid, upon analysis, proved to be N,N'-di-p-n-butoxyphenacylterephthalimide. Calculated for for $C_{32} H_{36} N_2O_6$: C 70.6; H 6.62; N 5.14%. Found: C 70.66, 70.41; H 6.68, 6.56; N 5.20, 5.14%. The nuclear magnetic resonance spectrum (A-60) in deuterodimethyl sulfoxide at 105°C clearly showed triplets centered at 0.87 and 3.94 ($CH_3 CH_2$ and $—O CH_2 CH_2—$), a singlet at 4.55 ($—COCH_2NH—$), an $A_2B_2$ aromatic quartet at 6.72, 6.86, 7.63 and 7.78 (terminal aromatic protons) and aromatic singlet at 7.69 (central aromatic ring).

1,4-Bis (5-p-n-butoxyphenyloxazol-2-yl)-Benzene

N,N'-di-p-n-butoxyphenacylterephthalimide (6.0 g) in phosphoryl chloride (280 ml) was refluxed overnight. Unreacted phosphoryl chloride was evaporated under reduced pressure. Yellow crystals (4.6 g — 82% yield) of 1,4-bis(5-p-n-butoxyphenyloxazol-2-yl)-benzene were obtained from 1.6 l of glacial acetic acid. Calculated for $C_{32} H_{32} N_2 O_4$: C 75.4; H 6.28; N 5.50. Found: C 75.21, 75.17; H 6.44, 6.37; N 5.24, 5.29. The melting point was 217°–217.5°C. Saturated solutions of 1,4-bis(5-p-n-butoxyphenyloxazol-2-yl)-benzene in dimethyl sulfoxide, dioxane and 2-methoxyethanol were prepared and pumped by means of a nitrogen laser. The dye lased in the blue to blue-green regions.

What is claimed is:

1. The chemical compound: 1,4-bis(5-p-n-butoxyphenyloxazol-2-yl)-benzene.

2. A method for preparing 1,4-bis(5-p-n-butoxyphenyloxazol-2-yl)-benzene comprising the steps of:

a. reacting p-n butoxyacetophenone in solution with bromine stirred in slowly at room temperature to form p-n-butoxyphenacyl bromide;

b. reacting at room temperature said bromide in solution with hexamethylene tetramine in chloroform to form a quaternary salt of p-n-butoxyphenacyl bromide which is precipitated by stirring the solution into ether;

c. reacting said quaternary salt with hychochoric acid at room temperature to form after standing p-n-butoxyphenacylammonium chloride which is precipitated by stirring the solution into ether;

d. refluxing said chloride with terephthaloyl chloride in pyridine and chilling to form N,N' di-p-n-butoxyphenacylterephthalimide; and e. refluxing said imide with phosphoryl chloride to form said 1,4-bis(5-p-n-butoxyphenyl-oxazol-2-yl)-benzene.

* * * * *